US00PP25317P2

(12) United States Plant Patent
Heuger

(10) Patent No.: US PP25,317 P2
(45) Date of Patent: Feb. 24, 2015

(54) ***HELLEBORUS* PLANT NAMED 'COSEH 1060'**

(50) Latin Name: ***Helleborus niger*×*Helleborus lividus***
Varietal Denomination: COSEH 1060

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 117 days.

(21) Appl. No.: 13/815,556

(22) Filed: Mar. 8, 2013

(51) Int. Cl.
*A01H 5/00* (2006.01)

(52) U.S. Cl.
USPC ..... Plt./439

(58) Field of Classification Search
USPC ..... Plt./439
See application file for complete search history.

*Primary Examiner* — Susan McCormick Ewoldt
(74) *Attorney, Agent, or Firm* — C. A. Whealy

(57) ABSTRACT

A new and distinct cultivar of *Helleborus* plant named 'COSEH 1060', characterized by its upright and mounding plant habit; uniform and freely flowering habit; dark green-colored leaves; freely flowering habit; single white-colored flowers tinged with greyed red; and good garden performance.

2 Drawing Sheets

Botanical designation: *Helleborus niger*×*Helleborus lividus.*

Cultivar denomination: 'COSEH 1060'.

BACKGROUND OF THE INVENTION

The present invention relates to a new and distinct cultivar of *Helleborus* plant, botanically known as *Helleborus niger*× *Helleborus lividus* and hereinafter referred to by the name 'COSEH 1060'.

The new *Helleborus* plant is a product of a planned breeding program in Glandorf, Germany. The objective of the breeding program was to create new uniform *Helleborus* plants with unique and attractive plant habit, leaf and flower coloration and resistance to pests.

The new *Helleborus* plant originated from a cross-pollination conducted by the Inventor in Glandorf, Germany in December, 2006 of an unnamed proprietary seedling selection of *Helleborus niger*, not patented, as the female, or seed, parent with an unnamed proprietary seedling selection of *Helleborus lividus*, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in December, 2008.

Asexual reproduction of the new *Helleborus* plant by divisions in a controlled greenhouse environment in Glandorf, Germany since March, 2009 has shown that the unique features of this new *Helleborus* plant are stable and reproduced true to type in successive generations.

SUMMARY OF THE INVENTION

Plants of the new *Helleborus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 1060'. These characteristics in combination distinguish 'COSEH 1060' as a new and distinct *Helleborus* plant:

1. Upright and mounding plant habit.
2. Uniform and freely flowering habit.
3. Dark green-colored leaves.
4. Freely flowering habit.
5. Single white-colored flowers tinged with greyed red.
6. Good garden performance.

Compared to plants of the parent selections, plants of the new *Helleborus* are more uniformly mounded and are more freely flowering.

Plants of the new *Helleborus* can be compared to plants of *Helleborus niger*×*Helleborus lividus* 'COSEH 700', disclosed in U.S. Plant Pat. No. 21,003. In side-by-side comparisons conducted in Glandorf, Germany, plants of the new *Helleborus* differed primarily from plants of 'COSEH 700' in the following characteristics:

1. Plants of the new *Helleborus* had lighter green-colored leaves than plants of 'COSEH 700'.
2. Plants of the new *Helleborus* and 'COSEH 700' differed in sepal color as plants of 'COSEH 700' had light green-colored sepals tinged with greyed purple.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'COSEH 1060' grown in a container.

The photograph on the second sheet is a close-up view of a typical flower of 'COSEH 1060'.

DETAILED BOTANICAL DESCRIPTION

The aforementioned photographs and following observations, measurements and values describe plants grown during the late autumn in 15-cm containers in a glass-covered greenhouse in Glandorf, Germany and under cultural practices typical of commercial *Helleborus* production. During the production of the plants, day temperatures ranged from 12° C. to 32° C. and night temperatures ranged from 3° C. to 18° C. Plants were 14 months old when the photographs and the description were taken. In the following description, color references are made to The Royal Horticultural Society Colour Chart, 2007 Edition, except where general terms of ordinary dictionary significance are used.

Botanical classification: *Helleborus niger*×*Helleborus lividus* 'COSEH 1060'.

Parentage:

*Female, or seed, parent*.—Unnamed proprietary seedling selection of *Helleborus niger*, not patented.

*Male, or pollen, parent*.—Unnamed proprietary seedling selection of *Helleborus lividus*, not patented.

Propagation:

*Type*.—By tissue culture.

*Time to initiate roots, winter*.—About two months at temperatures about 12° C.

*Time to produce a rooted young plant, winter*.—About six months at temperatures about 4° C. to 15° C.

*Root description*.—Thick to thin, fleshy; white to brown in color.

*Rooting habit*.—Sparse.

Plant description:

*Plant and growth habit*.—Herbaceous perennial; upright and mounding plant habit with flowers held just above the foliar plane; plant shape is roughly globular to broadly ovate; low vigor to moderately vigorous growth habit.

*Plant height*.—About 23.9 cm.

*Plant diameter* (*area of spread*).—About 36.1 cm.

Foliage description:

*Arrangement*.—Leaves arranged in a basal rosette; leaves palmately compound with five leaflets per leaf.

*Leaf length*.—About 14.7 cm.

*Leaf width*.—About 17.4 cm.

*Leaflet length*.—About 9.2 cm.

*Leaflet width*.—About 3.8 cm.

*Leaf shape*.—Palmate; orbicular to reniform in outline.

*Leaflet shape*.—Elliptic to narrowly ovate and narrowly obovate.

*Leaflet apex*.—Acute.

*Leaflet base*.—Attenuate.

*Leaflet margin*.—Serrate.

*Leaflet texture, upper and lower surfaces*.—Smooth, glabrous; leathery.

*Leaflet venation pattern*.—Pinnate.

*Leaflet color*.—Developing leaves, upper surface: Close to 137A. Developing leaves, lower surface: Close to 148A. Fully developed leaves, upper surface: Darker than between 147A and N189A; venation, close to 144A, at the base, strongly tinged with close to 200A to 200B. Fully developed leaves, lower surface: Close to 148B; venation, close to 183B.

*Petioles*.—Length: About 11.9 cm. Diameter: About 5 mm. Texture, upper and lower surfaces: Smooth, glabrous. Color, upper and lower surfaces: Close to 200C heavily dotted with close to 147D.

Flower description:

*Flower shape and habit*.—Single rotate flowers arranged in panicles; freely and uniform flowering habit with about twelve flowers per panicle and about 72 flowers and flower buds developing per plant; flowers facing mostly outwardly.

*Fragrance*.—None detected.

*Natural flowering season*.—Plants begin flowering about ten months after planting; plants flower from late autumn into the winter in Germany.

*Flower longevity on the plant*.—About ten days; flowers not persistent.

*Flower buds*.—Length: About 2.2 cm. Diameter: About 1.3 cm. Shape: Broadly ovate to oblong. Color: Close to 157D heavily tinged with close to 182B to 182D.

*Inflorescence height* (*including peduncle*).—About 22.9 cm.

*Inflorescence diameter*.—About 12.8 cm.

*Flower diameter*.—About 8.1 cm.

*Flower depth* (*height*).—About 3.8 cm.

*Petals*.—Transformed into nectaries.

*Sepals*.—Quantity and arrangement: Five, arranged in a single whorl. Length: About 4 cm. Width: About 3 cm. Shape: Broadly ovate. Apex: Obtuse to broad and bluntly acute. Base: Broadly cuneate. Margin: Entire. Texture, upper and lower surfaces: Smooth, glabrous. Color: When opening, upper surface: Close to 157C; towards the margins, close to 155C; lowest sepals, close to 145C with margins tinged with close to 182C. When opening, lower surface: Close to 155A and 157D; towards the base, tinged with close to 182D; lowest sepals, close to 182C. Fully opened, upper surface: Close to between 150D and 157C; lowest sepals, close to 182C tinged with close to 195A to 195B; with development, color becomes closer to 144B with margins tinged with close to 177D and lowest sepals becoming closer to 144B heavily tinged with close to 197B. Fully opened, lower surface: Close to 150D; towards the base, tinged with close to 182D; lowest sepals, close to 182B.

*Peduncles*.—Length: About 17.5 cm. Diameter: About 8 mm. Aspect: About 15° from vertical. Strength: Strong. Texture: Smooth, glabrous. Color: Close to 147D, heavily dotted with close to 184A to 184B.

*Pedicels*.—Length: About 2.5 cm. Diameter: About 3 mm. Aspect: About 30° from peduncle axis. Strength: Moderately strong. Texture: Smooth, glabrous. Color: Close to 147D, heavily dotted with close to 184B.

*Reproductive organs*.—Stamens: Quantity per flower: About 100. Filament length: About 1.6 cm. Filament color: Close to NN155D. Anther shape: Reniform. Anther length: About 2 mm. Anther color: Close to between 1B and 2B. Pollen amount: Scarce. Pollen color: Close to 2D. Pistils: Quantity per flower: About six. Pistil length: About 1.1 cm. Stigma shape: Club-shaped. Stigma color: Close to NN155D. Style length: About 1 cm. Style color: Close to NN155D. Ovary color: Close to 145A to 145B. Nectaries (transformed petals): Quantity per flower: About 15. Length: About 1.1 cm. Diameter: About 3.5 mm. Shape: Narrowly triangular, flattened tubular. Color, immature, inner and outer surfaces: Close to 144C. Color, mature, inner and outer surfaces: Close to N144A; towards the apex, close to 154B; with development, color becoming closer to 151A with apices, closer to 151D.

*Seeds and fruits*.—Seed and fruit development have not been observed on plants of the new *Helleborus*.

Garden performance: Plants of the new *Helleborus* have been observed to have good garden performance and to tolerate rain, wind and high temperatures about 35° C. and to be hardy to USDA Hardiness Zone 5.

Pathogen & pest resistance: Plants of the new *Helleborus* have not been observed to be resistant to pathogens and pests common to *Helleborus* plants.

It is claimed:

1. A new and distinct *Helleborus* plant named 'COSEH 1060' as illustrated and described.

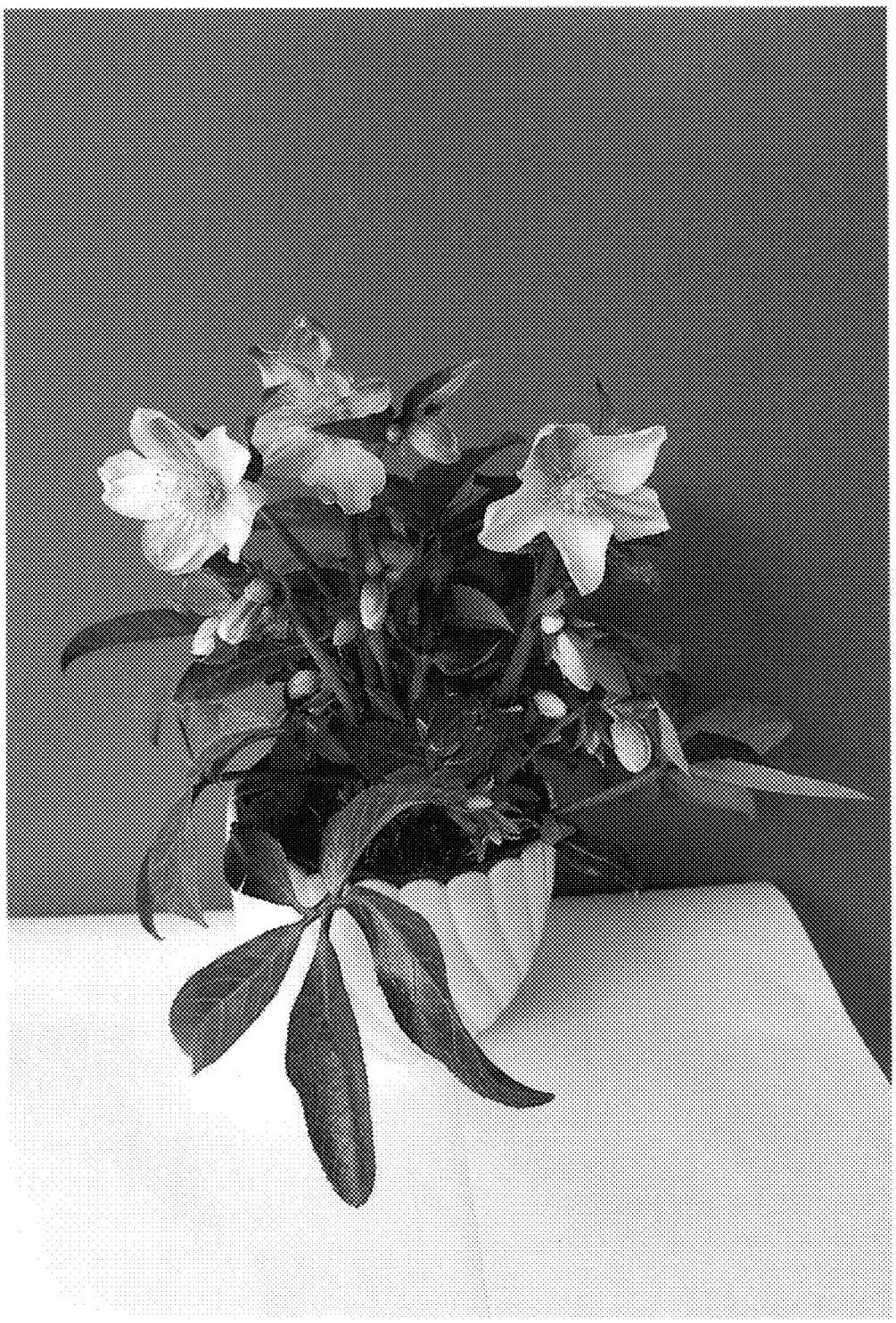

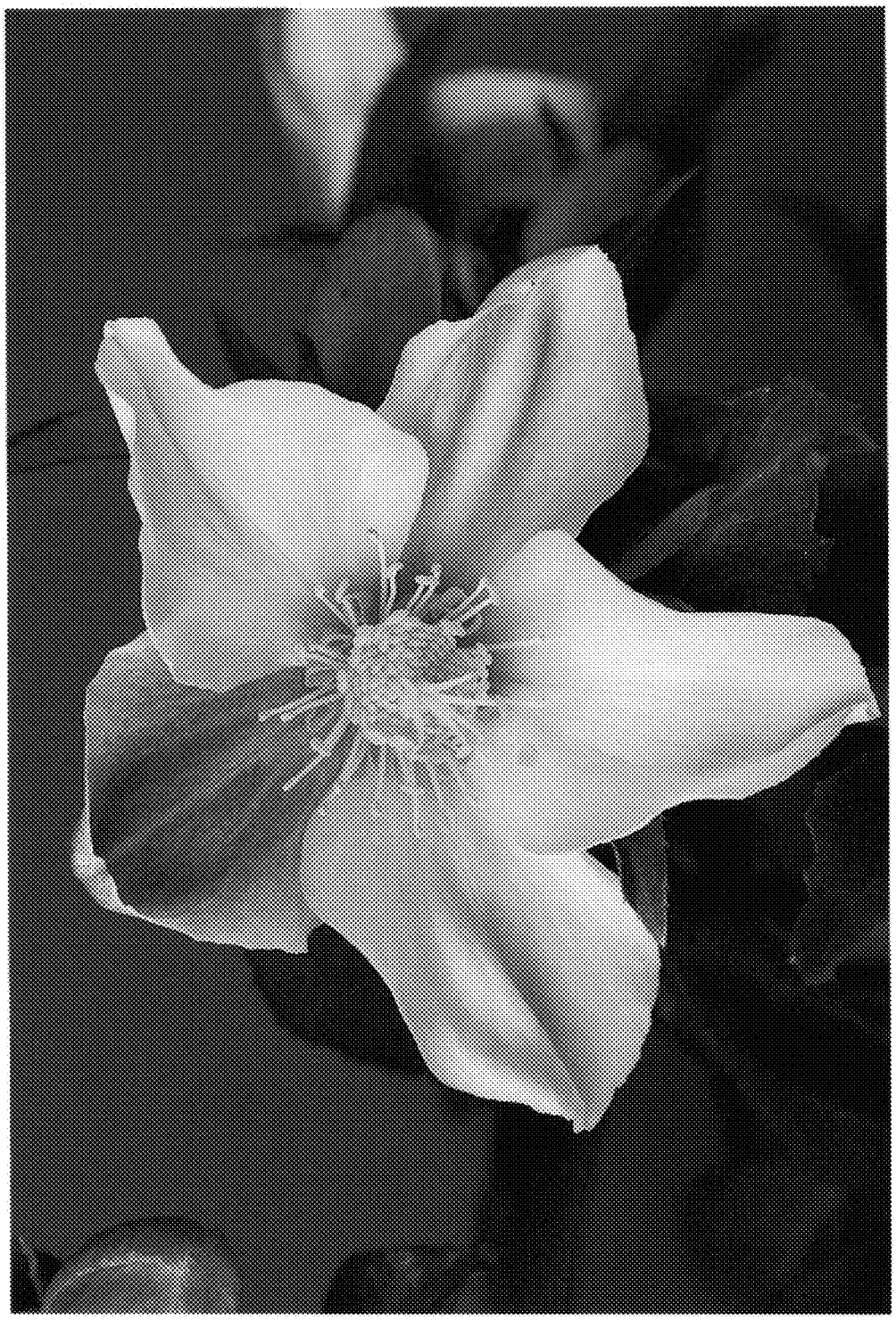

* * * * *